US012773351B2

(12) United States Patent
Sherman et al.

(10) Patent No.: US 12,773,351 B2
(45) Date of Patent: Oct. 27, 2026

(54) PACKAGED MEDICAL ARTICLES WITH REDUCED PACKAGING

(71) Applicant: Solventum Intellectual Properties Company, Maplewood, MN (US)

(72) Inventors: Audrey A. Sherman, Woodbury, MN (US); Christoph T.R. Schuell, Neuss (DE); Jess W. Smith, Apple Valley, MN (US); Hironobu Ishiwatari, Tokyo (JP)

(73) Assignee: Solventum Intellectual Properties Company, Maplewood, MN (US)

( * ) Notice: Subject to any disclaimer, the term of this patent is extended or adjusted under 35 U.S.C. 154(b) by 293 days.

(21) Appl. No.: 18/031,519

(22) PCT Filed: Oct. 20, 2021

(86) PCT No.: PCT/IB2021/059684
§ 371 (c)(1),
(2) Date: Apr. 12, 2023

(87) PCT Pub. No.: WO2022/084888
PCT Pub. Date: Apr. 28, 2022

(65) Prior Publication Data

US 2023/0372158 A1 Nov. 23, 2023

Related U.S. Application Data

(60) Provisional application No. 63/094,402, filed on Oct. 21, 2020.

(51) Int. Cl.
*A61F 13/00* (2024.01)
*A61F 9/04* (2006.01)
(Continued)

(52) U.S. Cl.
CPC .......... *A61F 13/0008* (2013.01); *A61F 9/045* (2013.01); *A61F 13/0253* (2013.01); *A61F 13/0259* (2013.01)

(58) Field of Classification Search
CPC .......... A61F 13/00; A61F 13/02; A61F 13/12; A61F 13/122; A61F 13/00655;
(Continued)

(56) References Cited

U.S. PATENT DOCUMENTS 3,645,835 A 2/1972 Hodgson
4,595,001 A 6/1986 Potter et al.
(Continued)

FOREIGN PATENT DOCUMENTS

EP 2377498 A1 * 10/2011 ......... A61F 13/0008
EP 3628287 A1 4/2020
(Continued)

OTHER PUBLICATIONS

JP 2006167055 A machine translation (Year: 2006).*
(Continued)

*Primary Examiner* — Caitlin A Carreiro

(57) ABSTRACT

A packaged medical article includes a package enclosing a medical article and a medical article contained within the package. The medical article is an adhesive article, where the adhesive article includes at least one fold along a fold line along an axis of symmetry of the adhesive article. Some of the folded adhesive articles have three segments, two adhesive segments and an absorbent pad, where the two adhesive segments are attached to a double sided release liner.

8 Claims, 3 Drawing Sheets

(51) Int. Cl.
*A61F 13/02* (2024.01)
*A61F 13/0246* (2024.01)

(58) Field of Classification Search
CPC .......... A61F 13/00676; A61F 13/00072; A61F 13/00076; A61F 13/0008; A61F 13/0253; A61F 13/0259; A61F 13/124; A61F 9/045
USPC .................................... 602/41, 57, 60, 61, 74
See application file for complete search history.

(56) References Cited

U.S. PATENT DOCUMENTS

| | | | | | |
|---|---|---|---|---|---|
| 4,793,003 | A | * | 12/1988 | Riedel | A61F 13/124 604/371 |
| 5,088,483 | A | | 2/1992 | Heinecke | |
| 5,160,315 | A | | 11/1992 | Heinecke et al. | |
| 5,214,119 | A | | 5/1993 | Leir et al. | |
| 5,461,134 | A | | 10/1995 | Leir et al. | |
| 5,512,650 | A | | 4/1996 | Leir et al. | |
| 6,630,554 | B1 | | 10/2003 | Hamada et al. | |
| 6,734,256 | B1 | | 5/2004 | Everaerts et al. | |
| 6,806,320 | B2 | | 10/2004 | Everaerts et al. | |
| 6,984,114 | B2 | | 1/2006 | Zili et al. | |
| 7,084,209 | B2 | | 8/2006 | Everaerts et al. | |
| 7,153,924 | B2 | | 12/2006 | Kuepfer et al. | |
| 7,255,920 | B2 | | 8/2007 | Everaerts et al. | |
| 9,738,818 | B2 | | 8/2017 | Sherman et al. | |
| 2007/0148475 | A1 | | 6/2007 | Sherman et al. | |
| 2009/0186183 | A1 | * | 7/2009 | Michel | B32B 27/10 428/41.3 |
| 2011/0212325 | A1 | | 9/2011 | Determan et al. | |
| 2012/0192330 | A1 | * | 8/2012 | McMullen | A41D 13/1184 2/9 |
| 2014/0246144 | A1 | | 9/2014 | Miyachika et al. | |

FOREIGN PATENT DOCUMENTS

| | | | | | |
|---|---|---|---|---|---|
| EP | 2377498 | B1 | | 5/2020 | |
| JP | H11302617 | A | | 11/1999 | |
| JP | H11323072 | A | | 11/1999 | |
| JP | 2006167055 | A | * | 6/2006 | |
| JP | 4598503 | B2 | * | 12/2010 | |
| WO | 199634028 | A1 | | 10/1996 | |
| WO | 199634030 | A1 | | 10/1996 | |
| WO | 199635458 | A2 | | 11/1996 | |
| WO | 199740103 | A1 | | 10/1997 | |
| WO | 199817726 | A1 | | 4/1998 | |
| WO | WO-2011035393 | A1 | * | 3/2011 | A61F 9/045 |
| WO | WO-2017058499 | A1 | * | 4/2017 | C08F 265/04 |
| WO | 2022013643 | A1 | | 1/2022 | |

OTHER PUBLICATIONS

JP 4598503 machine translation (Year: 2010).*
International Search Report for PCT International Application No. PCT/IB2021/059684, mailed on Feb. 1, 2022, 3 pages.

* cited by examiner

PACKAGED MEDICAL ARTICLES WITH REDUCED PACKAGING

FIELD OF THE DISCLOSURE

The current disclosure relates to medical articles contained within a package, where the medical article is folded to reduce the size of the package required to contain it.

BACKGROUND

A wide variety of medical articles are placed within packages to keep them sterile, clean, secure, and easier to handle. Examples of medical articles include dressings, bandages, and the like.

A dressing is a sterile pad or compress applied to a wound to promote healing and protect the wound from further harm. A dressing is designed to be in direct contact with the wound. Many modern dressings are self-adhesive.

Bandages are a piece of material to support a medical apparatus, such as wound dressings, or on its own, to administer support to the body. Bandages, additionally, can be used to inhibit bodily fluids from flowing, such as blood, lymph fluid, and more.

A wide variety of medical articles are placed within packages to keep them sterile, clean, secure, and easier to handle. When the medical article is desired to be used, it is typically removed from the package, and often the packaging is discarded.

SUMMARY

The current disclosure relates to medical articles contained within a package, where the medical article has a reduced size to reduce the size of the package required to contain it. Also disclosed are methods of using the medical articles.

In some embodiments, the packaged medical article comprises a package enclosing a medical article and a medical article contained within the package. The medical article comprises an adhesive article, where the adhesive article comprises at least one fold along a fold line along an axis of symmetry of the adhesive article.

In some embodiments, the packaged medical article comprises a package enclosing a medical article and a medical article contained within the package where the medical article comprises an adhesive article comprising at least three segments. In some embodiments, the first segment comprises a first adhesive layer, the second segment, adjacent to the first segment, comprises a non-adhesive layer, and the third segment, adjacent to the second segment, comprises a second adhesive layer. The adhesive article also has one fold along a fold line along an axis of symmetry of the adhesive article, where the fold line is located in the second segment. The adhesive article also has a double-sided release liner with a first release surface and a second release surface, where the first release surface is in contact with adhesive layer of the first segment, and the second release surface is in contact with the second adhesive layer of the third segment.

In other embodiments, the packaged medical article comprises a package enclosing a medical article and a medical article contained within the package. The medical article comprises a double-sided release liner with a first release surface with a first release coating and a second release surface with a second release coating, where the first and second release coatings may be the same or different, a first adhesive article attached to the first release surface of the double-sided release liner, and a second adhesive article attached to the second release surface of the double-sided release liner.

Also disclosed are methods of using packaged medical articles. In some embodiments, the method comprises preparing a packaged medical article, opening the package, removing the medical article from the package, unfolding the medical article, and applying the medical article to mammalian skin. The packaged medical article comprises a medical article as described above.

BRIEF DESCRIPTION OF THE DRAWINGS

The present application may be more completely understood in consideration of the following detailed description of various embodiments of the disclosure in connection with the accompanying drawings.

Figure 1:
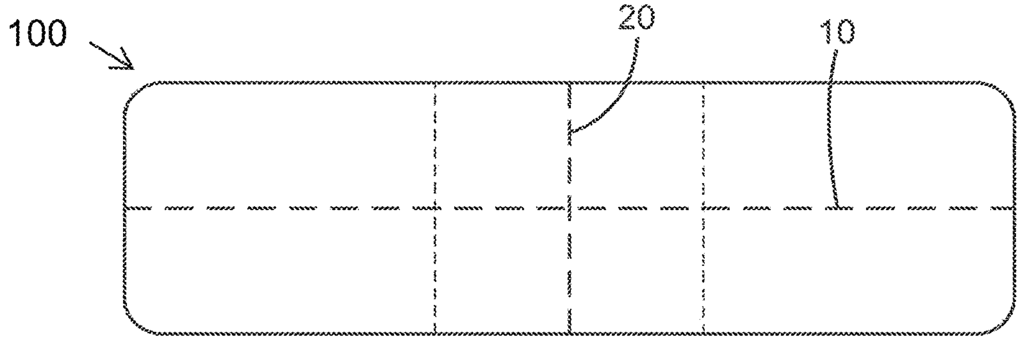
FIG. 1 is a top view of an adhesive medical article of this disclosure.

In the following description of the illustrated embodiments, reference is made to the accompanying drawings, in which is shown by way of illustration, various embodiments in which the disclosure may be practiced. It is to be understood that the embodiments may be utilized and structural changes may be made without departing from the scope of the present disclosure. The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Roughly one third of all dumps in the US is packaging material. A wide variety of techniques have been used to reduce the generation of waste from packaging. These techniques include recycling practices, and methods to reduce the size of packages by reducing the amount of empty space within packages. Additionally, supplies of packaged articles are generally shipped and stored in boxes or crates. These boxes or crates require storage space in facilities where storage space is often at a premium. Therefore, not only is desirable to reduce the amount of packaging material to reduce waste, but also reducing the size of articles reduces the amount of storage space required to ship and store the articles. This reduction in size for the articles permits either the use of smaller boxes or crates, or the inclusion of more articles in the currently used box or crate.

A wide variety of medical articles are placed within packages to keep them sterile, clean, secure, and easier to handle. Examples of medical articles include dressings, bandages, and eye patches.

A dressing is a sterile pad or compress applied to a wound to promote healing and protect the wound from further harm. A dressing is designed to be in direct contact with the wound. Many modern dressings are self-adhesive.

Bandages are a piece of material to support a medical apparatus, such as wound dressings, or on its own, to administer support to the body. Bandages, additionally, can be used to inhibit bodily fluids from flowing, such as blood, lymph fluid, and more.

As used herein, the term "eyepatch" is used to describe all medical eye coverings including eyepatches and eyepads. An eyepatch is a small patch that is worn in front of one eye. An eyepad or eye pad is a soft medical dressing that can be applied over an eye to protect it, keep it closed, or protect it from entering light. Eyepatches may be made of cloth or a polymeric material. Eyepatches are often worn by people to cover a lost or injured eye, but they also have a therapeutic use in children for the treatment of amblyopia.

When the medical article is desired to be used, it is typically removed from the package, and often the packaging is discarded. This produces waste that needs to be disposed of. If the packaging comes in contact with bodily fluids, the waste becomes medical waste which often has special handling requirements.

It would be desirable to have packaged medical articles that retain all of the desirable features of being packaged, such as sterility, cleanliness, security, and ease of handling, with a reduction in the amount of waste generated when the packaged medical article is used. Also, as discussed above, by reducing the size of a packaged article, one can reduce the size of a receptacle used to ship or store the articles. Typically, an ample supply of medical articles is needed at medical facilities, but storage space at such facilities is limited. Therefore, if one could reduce the size of packaged medical articles, one can store more medical articles in the same storage space.

In this disclosure, methods for preparing medical articles in a package are described where the medical articles have reduced packaging. In some embodiments, the medical articles are folded along a fold line along an axis of symmetry of the medical article to decrease the size of the package and the amount of packaging material needed to make the package. In other embodiments, double-sided release liners are used to reduce the size of the package. It has been discovered that a wide range of medical articles can be folded, unpackaged, and used with no ill effects to the medical article.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. For example, reference to "a layer" encompasses embodiments having one, two or more layers. As used in this specification and the appended claims, the term "or" is generally employed in its sense including "and/or" unless the content clearly dictates otherwise.

The term "adhesive" as used herein refers to polymeric compositions useful to adhere together two adherends. Examples of adhesives are non-tacky adhesives (i.e., cold-seal adhesives), heat activated adhesives, pressure sensitive adhesives, curable adhesives, and gel adhesives.

Non-tacky adhesives have limited or low tack to most substrates but can have acceptable adhesive strength when paired with specific target substrates or when two layers of the non-tacky adhesives are contacted. The non-tacky adhesive adheres by affinity.

Heat activated adhesives are non-tacky at room temperature but become tacky and capable of bonding to a substrate at elevated temperatures. These adhesives usually have a Tg or melting point (Tm) above room temperature. When the temperature is elevated above the Tg or Tm, the storage modulus usually decreases and the adhesive become tacky.

Pressure sensitive adhesive (PSA) compositions are well known to those of ordinary skill in the art to possess properties including the following: (1) aggressive and permanent tack, (2) adherence with no more than finger pressure, (3) sufficient ability to hold onto an adherend, and (4) sufficient cohesive strength to be cleanly removable from the adherend. Materials that have been found to function well as PSAs are polymers designed and formulated to exhibit the requisite viscoelastic properties resulting in a desired balance of tack, peel adhesion, and shear holding power. Obtaining the proper balance of properties is not a simple process.

Curable adhesives are reactive compositions that upon activation or mixing begin to react and form an adhesive bond. Examples of curable adhesives include anaerobic adhesives such as cyanoacrylates that polymerize and form bonds upon exposure to oxygen, as well as 2-part adhesives where the 2 parts are mixed and react.

Hot melt adhesives are thermoplastic materials that are solid and non-tacky at room temperature but upon heating melt and flow. The hot melt adhesive is applied in the molten state and forms a bond upon cooling to a solid state.

As used herein, the term "gel adhesive" refers to a tacky semi-solid crosslinked matrix containing a liquid or a fluid that is capable of adhering to one or more substrates. The gel adhesives may have some properties in common with pressure sensitive adhesives, but they are not pressure sensitive adhesives. "Hydrogel adhesives" are gel adhesives that have water as the fluid contained within the crosslinked matrix.

The term "(meth)acrylate" refers to monomeric acrylic or methacrylic esters of alcohols. Acrylate and methacrylate monomers or oligomers are referred to collectively herein as "(meth)acrylates". Materials referred to as "(meth)acrylate functional" are materials that contain one or more (meth) acrylate groups.

The terms "siloxane-based" as used herein refer to polymers or units of polymers that contain siloxane units. The terms silicone or siloxane are used interchangeably and refer to units with dialkyl or diaryl siloxane ($-SiR_2O-$) repeating units.

The terms "room temperature" and "ambient temperature" are used interchangeably to mean temperatures in the range of 20° C. to 25° C.

The terms "Tg" and "glass transition temperature" are used interchangeably. If measured, Tg values are determined by Differential Scanning calorimetry (DSC) at a scan rate of 10° C./minute, unless otherwise indicated. Typically, Tg values for copolymers are not measured but are calculated using the well-known Fox Equation, using the homopolymer monomer Tg values provided by the monomer supplier, as is understood by one of skill in the art.

The term "adjacent" as used herein when referring to two layers means that the two layers are in proximity with one another with no intervening open space between them. They may be in direct contact with one another (e.g. laminated together) or there may be intervening layers.

The terms "polymer" and "macromolecule" are used herein consistent with their common usage in chemistry. Polymers and macromolecules are composed of many repeated subunits. As used herein, the term "macromolecule" is used to describe a group attached to a monomer that has multiple repeating units. The term "polymer" is used to describe the resultant material formed from a polymerization reaction.

The term "alkyl" refers to a monovalent group that is a radical of an alkane, which is a saturated hydrocarbon. The alkyl can be linear, branched, cyclic, or combinations thereof and typically has 1 to 20 carbon atoms. In some embodiments, the alkyl group contains 1 to 18, 1 to 12, 1 to 10, 1 to 8, 1 to 6, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

The term "aryl" refers to a monovalent group that is aromatic and carbocyclic. The aryl can have one to five rings that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

The terms "free radically polymerizable" and "ethylenically unsaturated" are used interchangeably and refer to a reactive group which contains a carbon-carbon double bond which is able to be polymerized via a free radical polymerization mechanism.

Unless otherwise indicated, the terms "optically transparent", and "visible light transmissive" are used interchangeably, and refer to an article, film or adhesive that has a high light transmittance over at least a portion of the visible light spectrum (about 400 to about 700 nm). Typically, optically transparent articles have a visible light transmittance of at least 80% and a haze of less than 10%.

Unless otherwise indicated, "optically clear" refers to an adhesive or article that has a high light transmittance of at least 90% over at least a portion of the visible light spectrum (about 400 to about 700 nm), and that exhibits low haze, typically less than about 5%, or even less than about 2%.

Disclosed herein are packaged articles. In some embodiments, the packaged articles comprise a package enclosing a medical article, and a medical article contained within the package. The medical article comprises an adhesive article, where the adhesive article comprises at least one fold along a fold line along an axis of symmetry of the adhesive article.

Other packaged articles of this disclosure comprise a double-sided release liner to reduce the size of the article to be packaged. In some embodiments, the adhesive articles are folded and adhered to the double-sided release liner, in other embodiments two adhesive articles are adhered to the opposite sides of the double-sided release liner. These articles are described in greater detail below.

A wide variety of packages are suitable for use in the packaged articles of the present disclosure. Packages as used herein are containers having a first substrate layer and a second substrate layer where the entire perimeter of contact between the first substrate layer and second substrate layer is sealed to give a discrete sealed unit.

A wide variety of materials can be used in the first and second substrate layers. The first and second substrate layers may be the same or they may be different. Examples of suitable substrates include paper, polymer-coated paper, nonwovens, polymeric films and metal foils. Examples of suitable metal foils include aluminum foil. Examples of polymeric films include films comprising one or more polymers such as cellulose acetate butyrate; cellulose acetate propionate; cellulose triacetate; poly(meth)acrylates such as polymethyl methacrylate; polyesters such as polyethylene terephthalate, and polyethylene naphthalate; copolymers or blends based on naphthalene dicarboxylic acids; polyether sulfones; polyurethanes; polycarbonates; polyvinyl chloride; syndiotactic polystyrene; cyclic olefin copolymers; and polyolefins including polyethylene and polypropylene such as cast and biaxially oriented polypropylene. The substrate may comprise single or multiple layers, such as polyethylene-coated polyethylene terephthalate. The substrate may be primed or treated to impart some desired property to one or more of its surfaces. Examples of such treatments include corona, flame, plasma and chemical treatments.

The two substrates can be sealed in a wide variety of ways, depending upon the materials comprising the substrates as well as the desired use for the packaged article. In embodiments where the substrates are polymeric or contain polymeric coatings, the packages can be sealed by melt sealing by the use of heat and pressure. In other embodiments, the packages are adhesively sealed. A wide variety of adhesives are suitable including non-tacky adhesives (i.e., cold-seal adhesives), heat activated adhesives, pressure sensitive adhesives, cured adhesives, and hot melt adhesives.

Non-tacky adhesives have limited or low tack to most substrates but can have acceptable adhesive strength when paired with specific target substrates or when two layers of the non-tacky adhesives are contacted. The non-tacky adhesive adheres by affinity.

Heat activated adhesives are non-tacky at room temperature but become tacky and capable of bonding to a substrate at elevated temperatures. These adhesives usually have a Tg or melting point (Tm) above room temperature. When the temperature is elevated above the Tg or Tm, the storage modulus usually decreases and the adhesive become tacky.

Pressure sensitive adhesive (PSA) compositions are well known to those of ordinary skill in the art to possess properties including the following: (1) aggressive and permanent tack, (2) adherence with no more than finger pressure, (3) sufficient ability to hold onto an adherend, and (4) sufficient cohesive strength to be cleanly removable from the adherend. Materials that have been found to function well as PSAs are polymers designed and formulated to exhibit the requisite viscoelastic properties resulting in a desired balance of tack, peel adhesion, and shear holding power. Obtaining the proper balance of properties is not a simple process.

Curable adhesives are reactive compositions that upon activation or mixing begin to react and form an adhesive bond. Examples of curable adhesives include anaerobic adhesives such as cyanoacrylates that polymerize and form bonds upon exposure to oxygen, as well as 2-part adhesives where the 2 parts are mixed and react. Examples of 2-part adhesives include epoxy and urethane adhesives. Two-part epoxy adhesives have epoxy resins in one part and epoxy curatives in the second part. Two=part urethane adhesives have polyols in one part and polyisocyanates in the second part, and may also include a curing catalyst.

Hot melt adhesives are thermoplastic materials that are solid and non-tacky at room temperature but upon heating melt and flow. The hot melt adhesive is applied in the molten state and forms a bond upon cooling to a solid state.

The choice of method of sealing depends upon a variety of factors, including the needs to environment exposure conditions that the package is to be exposed (such a humidity, heat, etc.), the length of time the package needs to remain sealed, and the desired ease of opening of the package.

A wide range of adhesive medical articles are suitable for use in the packaged articles of this disclosure. In some embodiments, the adhesive article is a planar article. Planar articles are those that are defined by two primary dimensions a length and a width. Mathematically, these dimensions can be defined by axes, with the length being the x axis and the width being the y axis. Of course, the articles are in fact three dimensional objects and have a third dimension, which is the thickness and mathematically is defined as the z axis.

The articles are not necessarily in the shape of a regular polygon, i.e. the article may not be in the shape of a square or rectangle for example. The sides of the article may be curved or angled. Because of the variety of shapes of the articles, the articles can have a variety of axes of symmetry. These axes of symmetry can be along the x axis, along the y axis, or can form a variety of angles from the x axis or y axis.

In some embodiments, the planar adhesive article has a length (x axis) and a width (y axis) and the one fold along a fold line along an axis of symmetry comprises a fold along the y axis. In this way, the folded article has half the length of the unfolded article. This decrease in length is achieved by a doubling of the thickness of the article. However, since the thickness of the article is so much less than the length of the article, and since the substrates of the package are flexible, this doubling of thickness does not require a significant change of the thickness of the package. Thus, the package can be half the length and substantially the same thickness as the package that contains the same article in an unfolded state.

In some embodiments, the planar article has a length (x axis) and a width (y axis) and the one fold along a fold line along an axis of symmetry comprises a fold along the x axis. In this way, the folded article has half the width of the unfolded article. This decrease in width is achieved by a doubling of the thickness of the article. However, since the thickness of the article is so much less than the width of the article, and since the substrates of the package are flexible, this doubling of thickness does not require a significant change of the thickness of the package. Thus, the package can be half the width and substantially the same thickness as the package that contains the same article in an unfolded state.

A wide variety of adhesive medical articles are suitable for preparing the packaged medical articles of this disclosure. Among the suitable articles are wound dressings. Wound dressings comprise a backing layer, an adhesive layer that may be continuous or discontinuous, and optionally may include an absorbent pad.

The backing layer is rigid enough to provide stability to the adhesive article but remains flexible. Examples of suitable tape backings include breathable conformable backing, on which the adhesive layer is disposed. A wide range of breathable conformable backings are suitable for use in articles of this disclosure. Examples of breathable conformable backing include woven or knit textiles, nonwovens, or a polymeric films.

In some embodiments, the breathable conformable backing comprises a high moisture vapor permeable film backing. Examples of such backings, methods of making such films, and methods for testing their permeability are described, for example, in U.S. Pat. Nos. 3,645,835 and 4,595,001. Typically, such backings are porous materials.

Generally, the backing is conformable to anatomical surfaces. As such, when the backing is applied to an anatomical surface, it conforms to the surface even when the surface is moved. Generally, the backing is also conformable to animal anatomical joints. When the joint is flexed and then returned to its unflexed position, the backing stretches to accommodate the flexion of the joint, but is resilient enough to continue to conform to the joint when the joint is returned to its unflexed condition.

Examples of particularly suitable backings can be found in U.S. Pat. Nos. 5,088,483 and 5,160,315, and include elastomeric polyurethane, polyester, or polyether block amide films. These films have a combination of desirable properties including resiliency, high moisture vapor permeability, and transparency.

As mentioned above, in some embodiments the backing layer is transparent (and used in conjunction with a transparent adhesive) to prepare a transparent dressing. Transparent dressings are most commonly used when a doctor wants to closely monitor healing of a specific wound. Since transparent dressings are made using a clear film, it's much easier to monitor wounds using this type of dressing in compared to a cloth or foam bandage. For this reason, transparent dressings are often used on larger, more complicated wounds.

The substrate layer has a wide range of thicknesses. In some embodiments, the thickness is at least 10 micrometers, up to 152 micrometers (6 mils), and in some embodiments the thickness will be from 25 micrometers (1 mil) up to 102 micrometers (4 mils) thick. A wide range of intermediate thicknesses are also suitable.

A wide variety of adhesives are suitable for used in the adhesive layers of the articles of this disclosure. Typically, the adhesive layer comprises a pressure sensitive adhesive or a gel adhesive. Among the suitable pressure sensitive adhesives are (meth)acrylate pressure sensitive adhesives, siloxane pressure sensitive adhesives, and block copolymer pressure sensitive adhesives. The pressure sensitive adhesive may contain a single polymeric material or may contain a blend of polymeric materials. The pressure sensitive adhesive may be a crosslinked pressure sensitive adhesive. Examples of suitable gel adhesives are siloxane gel adhesives which comprise a crosslinked siloxane matrix and a fluid, typically a siloxane fluid. Each of these adhesives is described in detail below.

In some embodiments the adhesive is a (meth)acrylate-based pressure sensitive adhesive. Particularly suitable (meth)acrylate-based pressure sensitive adhesives include copolymers derived from: (A) at least one monoethylenically unsaturated alkyl (meth) acrylate monomer (i.e., alkyl acrylate and alkyl methacrylate monomer); and (B) at least one monoethylenically unsaturated free-radically copolymerizable reinforcing monomer. The reinforcing monomer has a homopolymer glass transition temperature (Tg) higher than that of the alkyl (meth)acrylate monomer and is one that increases the glass transition temperature and cohesive strength of the resultant copolymer. Herein, "copolymer" refers to polymers containing two or more different monomers, including terpolymers, tetrapolymers, etc.

Monomer A, which is a monoethylenically unsaturated alkyl acrylate or methacrylate (i.e., (meth)acrylic acid ester), contributes to the flexibility and tack of the copolymer. Generally, monomer A has a homopolymer Tg of no greater than about 0° C. Typically, the alkyl group of the (meth) acrylate has an average of about 4 to about 20 carbon atoms, or an average of about 4 to about 14 carbon atoms. The alkyl group can optionally contain oxygen atoms in the chain thereby forming ethers or alkoxy ethers, for example. Examples of monomer A include, but are not limited to, 2-methylbutyl acrylate, isooctyl acrylate, lauryl acrylate, 4-methyl-2-pentyl acrylate, isoamyl acrylate, sec-butyl acrylate, n-butyl acrylate, n-hexyl acrylate, 2-ethylhexyl acrylate, n-octyl acrylate, n-decyl acrylate, isodecyl acrylate, isodecyl methacrylate, and isononyl acrylate. Other examples include, but are not limited to, poly-ethoxylated or -propoxylated methoxy (meth)acrylates such as acrylates of CARBOWAX (commercially available from Union Carbide) and NK ester AM90G (commercially available from Shin Nakamura Chemical, Ltd., Japan). Suitable monoethylenically unsaturated (meth)acrylates that can be used as monomer A include isooctyl acrylate, 2-ethyl-hexyl acrylate, and n-butyl acrylate. Combinations of various monomers categorized as an A monomer can be used to make the copolymer.

Monomer B, which is a monoethylenically unsaturated free-radically copolymerizable reinforcing monomer, increases the glass transition temperature and cohesive strength of the copolymer. Generally, monomer B has a homopolymer Tg of at least about 10° C. Typically, monomer B is a reinforcing (meth)acrylic monomer, including an acrylic acid, a methacrylic acid, an acrylamide, or a (meth) acrylate. Examples of monomer B include, but are not limited to, acrylamides, such as acrylamide, methacrylamide, N-methyl acrylamide, N-ethyl acrylamide, N-hydroxyethyl acrylamide, diacetone acrylamide, N,N-dimethyl acrylamide, N, N-diethyl acrylamide, N-ethyl-N-aminoethyl acrylamide, N-ethyl-N-hydroxyethyl acrylamide, N,N-dihydroxyethyl acrylamide, t-butyl acrylamide, N,N-dimethylaminoethyl acrylamide, and N-octyl acrylamide. Other examples of monomer B include itaconic acid, crotonic acid, maleic acid, fumaric acid, 2,2-(diethoxy)ethyl acrylate, 2-hydroxyethyl acrylate or methacrylate, 3-hydroxypropyl acrylate or methacrylate, methyl methacrylate, isobornyl acrylate, 2-(phenoxy)ethyl acrylate or methacrylate, biphenylyl acrylate, t-butylphenyl acrylate, cyclohexyl acrylate, dimethyladamantyl acrylate, 2-naphthyl acrylate, phenyl acrylate, N-vinyl formamide, N-vinyl acetamide, N-vinyl pyrrolidone, and N-vinyl caprolactam. Particularly suitable reinforcing acrylic monomers that can be used as monomer B include acrylic acid and acrylamide. Combinations of various reinforcing monoethylenically unsaturated monomers categorized as a B monomer can be used to make the copolymer.

Generally, the (meth)acrylate copolymer is formulated to have a resultant Tg of less than about 0° C. and more typically, less than about −10° C. Such (meth)acrylate copolymers generally include about 60 parts to about 98 parts per hundred of at least one monomer A and about 2 parts to about 40 parts per hundred of at least one monomer B. In some embodiments, the (meth)acrylate copolymers have about 85 parts to about 98 parts per hundred or at least one monomer A and about 2 parts to about 15 parts of at least one monomer B.

In other embodiments, the adhesive comprises a siloxane pressure sensitive adhesive. A wide variety of siloxane pressure sensitive adhesives are suitable, and typically are referred to as siloxane-based, as the pressure sensitive adhesives may contain additional groups besides siloxane units. The siloxane-based pressure sensitive adhesive compositions comprise at least one siloxane-based elastomeric polymer and typically include tackifying resins. Examples of suitable siloxane-based elastomeric polymers include for example, urea-containing siloxane copolymers, oxamide-containing siloxane copolymers, amide-containing siloxane copolymers, urethane-containing siloxane copolymers, and mixtures thereof. Siloxane-based pressure sensitive adhesives are different from the siloxane gel adhesives described below since pressure sensitive adhesives and gel adhesives are different classes of materials.

Useful silicone polyurea block copolymers are disclosed in, e.g., U.S. Pat. Nos. 5,512,650, 5,214,119, 5,461,134, and 7,153,924 and PCT Publication Nos. WO 96/35458, WO 98/17726, WO 96/34028, WO 96/34030 and WO 97/40103.

Another useful class of silicone elastomeric polymers are oxamide-containing polymers such as polydiorganosiloxane polyoxamide block copolymers. Examples of polydiorganosiloxane polyoxamide block copolymers are presented, for example, in US Patent Publication No. 2007-0148475.

Another useful class of silicone elastomeric polymers is amide-based silicone polymers. Such polymers are similar to the urea-based polymers, containing amide linkages (—N(D)-C(O)—) instead of urea linkages (—N(D)-C(O)—N(D)-), where C(O) represents a carbonyl group and D is a hydrogen or alkyl group.

Such polymers may be prepared in a variety of different ways. Starting from the polydiorganosiloxane diamine described above in Formula II, the amide-based polymer can be prepared by reaction with a poly-carboxylic acid or a poly-carboxylic acid derivative such as, for example diesters. In some embodiments, an amide-based silicone elastomer is prepared by the reaction of a polydiorganosiloxane diamine and di-methyl salicylate of adipic acid.

Another useful class of silicone elastomeric polymers is urethane-containing silicone polymers such as silicone polyurea-urethane block copolymers. Silicone polyurea-urethane block copolymers include the reaction product of a polydiorganosiloxane diamine (also referred to as silicone diamine), a diisocyanate, and an organic polyol. Such materials are structurally very similar to the structure of Formula I except that the —N(D)-B—N(D)- links are replaced by —O—B—O— links. Examples are such polymers are presented, for example, in U.S. Pat. No. 5,214,119.

The siloxane block copolymer adhesives typically include a siloxane tackifying resin. Siloxane tackifying resins have in the past been referred to as "silicate" tackifying resins, but that nomenclature has been replaced with the term "siloxane tackifying resin". The siloxane tackifying resins are added in sufficient quantity to achieve the desired tackiness and level of adhesion. In some embodiments, a plurality of siloxane tackifying resins can be used to achieve desired performance.

Suitable siloxane tackifying resins include MQ siloxane tackifying resins. Suitable siloxane tackifying resins are commercially available from sources such as Dow Corning (e.g., DC 2-7066), Momentive Performance Materials (e.g., SR545 and SR1000), and Wacker Chemie AG (e.g., BELSIL TMS-803).

In other embodiments, the adhesive comprises a block copolymer pressure sensitive adhesive that are not siloxane-based like the polymers described above. Examples of suitable block copolymers comprise polyurethane block copolymers, polyurea block copolymers, or hydrocarbon block copolymers.

Examples of suitable polyurethane block copolymers and polyurea block copolymers include the non-siloxane polymers described in U.S. Pat. No. 9,738,818.

Another suitable class of block copolymer pressure sensitive adhesives is hydrocarbon-based block copolymer pressure sensitive adhesives. Examples of suitable hydrocarbon-based block copolymer pressure sensitive adhesives are styrene block copolymer pressure sensitive adhesives and (meth)acrylate block copolymer pressure sensitive adhesives.

Styrene block copolymer pressure sensitive adhesives generally comprise elastomers of the A-B or A-B-A type, where A represents a thermoplastic polystyrene block and B represents a rubbery block of polyisoprene, polybutadiene, or poly(ethylene/butylene), and resins. Examples of the various block copolymers useful in block copolymer pressure sensitive adhesives include linear, radial, star and tapered styrene-isoprene block copolymers such as "KRATON D1107P", available from KRATON Corp., and "EUROPRENE SOL TE 9110", available from EniChem Elastomers Americas, Inc.; linear styrene-(ethylene-butylene) block copolymers such as "KRATON G1657", available from KRATON Corp.; linear styrene-(ethylene-propylene) block copolymers such as "KRATON G1750X", available from KRATON Corp.; and linear, radial, and star styrene-butadiene block copolymers such as "KRATON D1118X", available from KRATON Corp., and "EUROPRENE SOL TE 6205", available from EniChem Elastomers Americas, Inc. The polystyrene blocks tend to form domains in the shape of spheroids, cylinders, or plates that causes the block copolymer pressure sensitive adhesives to have two phase structures.

Also suitable are (meth)acrylate-based block copolymer pressure sensitive adhesives. The (meth)acrylate-based block pressure sensitive adhesives include copolymers that are the reaction product of at least two A block polymeric units and at least one B block polymeric unit (i.e., at least two A block polymeric units are covalently bonded to at least one B block polymeric unit). Each A block, which has a Tg of at least 50° C., is the reaction product of a first monomer composition that contains an alkyl methacrylate, an aralkyl methacrylate, an aryl methacrylate, or a combination thereof. The B block, which has a Tg no greater than 20° C., is the reaction product of a second monomer composition that contains an alkyl(meth)acrylate, a heteroalkyl(meth)acrylate, a vinyl ester, or a combination thereof. The block copolymer contains 20 to 50 weight percent A block and 50 to 80 weight percent B block based on the weight of the block copolymer.

Methods of preparing block copolymers using living anionic polymerization methods are further described, for example, in U.S. Pat. No. 6,734,256 (Everaerts et al), U.S. Pat. No. 7,084,209 (Everaerts et al), U.S. Pat. No. 6,806,320 (Everaerts et al), and U.S. Pat. No. 7,255,920 (Everaerts et al.). This polymerization method is further described, for example, in U.S. Pat. No. 6,630,554 (Hamada et al.) and U.S. Pat. No. 6,984,114 (Kato et al.) as well as in Japanese Patent Application Kokai Publication Nos. Hei 11-302617 (Uchiumi et al.) and 11-323072 (Uchiumi et al.). Suitable block copolymers can be purchased from Kuraray Co., LTD. (Tokyo, Japan) under the trade designations LA POLYMER or KURARITY. Some of these block copolymers such as LA2140E, LA2250, LA2330, and LA410L are triblock copolymers with poly(methyl methacrylate) endblocks and a poly(n-butyl acrylate) midblock.

In some embodiments, the adhesive layer comprises a gel adhesive composition. Gel adhesives comprise a crosslinked polymeric siloxane matrix and a fluid, typically a siloxane fluid. A wide variety of crosslinked polymeric siloxane matrices are suitable for use in the gel adhesive compositions. The matrices can be prepared in a variety of ways. The crosslinked polymeric siloxane matrix can be prepared by thermal curing, condensation curing, radiation curing, or a combination thereof. Particularly suitable is the technique described, for example, in US Patent Publication No. 2011/0212325 (Determan et al.) in which polysiloxane fluids are crosslinked by exposure to E-beam radiation to form a polysiloxane matrix with the unpolymerized polysiloxane fluid forming the fluid component of the gel adhesive.

As with the siloxane pressure sensitive adhesives described above, the siloxane gel adhesives can include siloxane tackifying resin. Siloxane tackifying resins are described above.

As mentioned above, the adhesive layer may be continuous or discontinuous. The thickness of the coated adhesive layer, typically in the form of a liquid is in part dependent on the nature of the materials used and the specific properties desired, but those properties and the relationship of thickness to the properties is well understood in the art. Exemplary thicknesses of an adhesive layer may be in the range from about 0.05 to about 100 micrometers.

The wound dressing articles may also include an optional absorbent pad. Typically, the pad is designed to contact a wound and absorb exudate from the wound. Examples of suitable pad materials include cloth and cloth-like materials such as gauze and non-woven fabrics, or foams. Absorbent pad materials are readily known in the art.

The articles may include additional optional layers. In some embodiments, it may be desirable for there to be a primer layer between the backing layer and the adhesive layer. Generally, the primer layer comprises materials that are commonly referred to as "primers" or "adhesion promoters". Primers and adhesion promoters are materials that are applied as thin coatings on a surface and strongly adhere to the surface and provide a modified surface chemistry to the surface. Examples of suitable coating materials include polyamides, poly(meth)acrylates, chlorinated polyolefins, rubbers, chlorinated rubbers, polyurethanes, siloxanes, silanes, polyester, epoxies, polycarbodiimides, phenolics, and combinations thereof.

Typically, the adhesive layer is covered with a release liner to protect the adhesive layer until used. A wide range of release liners are suitable for use in the adhesive articles of this disclosure. A wide variety of release liners are suitable. Release liners are commonly used and well understood in the adhesive arts. Exemplary release liners include those prepared from paper (e.g., Kraft paper) or polymeric material (e.g., polyolefins such as polyethylene or polypropylene, ethylene vinyl acetate, polyurethanes, polyesters such as polyethylene terephthalate, and the like, and combinations thereof). At least some release liners are coated with a layer of a release agent such as a silicone-containing material or a fluorocarbon-containing material. Exemplary release liners include, but are not limited to, liners commercially available from CP Film (Martinsville, Va.) under the trade designation "T-30" and "T-10" that have a silicone release coating on polyethylene terephthalate film.

The above described packaged articles are typical planar adhesive articles that are folded prior to placement in a package. In some embodiments, the regular processing steps to prepare the article are followed, and the prepared article is then folded for packaging. In this way, currently used processes can be used to form the folded articles of this disclosure. In these embodiments, the folding permits a reduction in the amount of packaging material necessary to make the packaged article. Also disclosed herein are packaged medical articles that are not simply folded versions of planar articles.

In some embodiments of the articles that are not simply folded versions of planar articles, the articles utilize double-sided release liners. Double-sided release liners are well known in the adhesive arts, and are release liners as described above, with release coatings on both major surfaces of the release liner. The release coatings may be the same or they may be different. Two classes of adhesive articles disclosed herein use double-sided release liners. The first class of articles are folded articles, where the article is folded such that two surfaces of the article are folded such that the two surfaces of the article contact the two release surfaces of the double-sided release liner. The second class of adhesive articles that use a double-sided release liner are articles that have two separate elements disposed on the two release surfaces of the double-sided release liner.

A wide variety of different articles of the first class of articles are disclosed. In some embodiments, the packaged medical article comprises a package enclosing a medical article, and a medical article contained within the package where the medical article comprises an adhesive article comprising a backing layer that has at least three segments. The three segments are a first segment comprising a first adhesive layer, a second segment, adjacent to the first segment, comprising a non-adhesive layer, and a third segment, adjacent to the second segment, comprising a second adhesive layer. The adhesive article has one fold along a fold line along an axis of symmetry of the adhesive article, where the one fold is located in the second segment. The adhesive article also comprises a double-sided release liner with a first release surface and a second release surface, where the first release surface is in contact with adhesive layer of the first segment, and the second release surface is in contact with the second adhesive layer of the third segment.

The second segment may be a very thin segment and may comprise a non-adhesive line along the axis of symmetry that permits the folding of the article. In other embodiments, the segment is larger and may comprise uncoated backing or it may include, for example an absorbent pad as described above.

The adhesive layer on the first segment may be the same or different from the adhesive layer on the third segment. Each also may be a continuous or a discontinuous coating of adhesive. Suitable adhesives are described above in detail.

Double sided release liners have been described above, with release coatings on both major surfaces of the release liner. The release coatings may be the same or they may be different. The selection of release coatings on the double-sided release liner depends upon a wide variety of factors. For example, if the adhesive coatings on the first segment and the second segment are the same, the release coatings may be the same or they may be different. One may wish to have different release coatings in this scenario, because the different release coatings are expected to give different release forces to the same adhesive, and thus one release coating will more easily release from its adhesive layer than the other identical adhesive layer. This permits one adhesive layer to be easily exposed while the release liner remains adhered to the second adhesive layer. A similar feature can be achieved through the use of two different adhesive layers and the same release coating on the double-sided release liner.

A wide variety of articles of the second class of articles are disclosed. These articles reduce the amount of packaging by including two articles in the same package by using both sides of the double-sided release liner. In these embodiments, the two articles may be the same or they may be different.

In some embodiments, the packaged medical article comprises a package enclosing a medical article, and a medical article contained within the package where the medical article comprises a double-sided release liner and two adhesive articles adhered to the double-sided release liner. The double-sided release liner has a first release surface with a first release coating and a second release surface with a second release coating, where the first and second release coatings may be the same or different. The first adhesive article is attached to the first release surface of the double-sided release liner, and the second adhesive article is attached to the second release surface of the double-sided release liner. The first and second adhesive articles may be the same or they may be different.

One particular suitable embodiment of the second class of articles are eye patches. Eye patches include an adhesive to hold the patch over the eye. In some embodiments, the eye patch article comprises two eye patches, one disposed on each release surface of the double-sided release liner. In this way, a health care worker that is covering the eyes of a patient is able to use a single package to cover both eyes. In other embodiments, the packaged article can have different articles disposed on the two release surfaces of the double-sided release liner. For example, an eye patch may be disposed on one of the surfaces of the double-sided release liner and a different adhesive article, such as an attachment article, can be disposed on the second surface of the double-sided release liner, such that the attachment article is available to help to secure the eye patch in place.

Other embodiments of articles that are not simply folded embodiments of planar articles, are articles that specifically designed to be folded. These embodiments include articles where the fold line comprises a gap or division in part of the article, such as the absorbent pad. The gap or division can be imparted in the article by, for example, by cutting or slitting. The gap or division does not pass through the entire article so that the article is not sub-divided into two articles.

Also disclosed herein are methods of making and using packaged medical articles. In some embodiments, the methods comprise preparing a packaged medical article, wherein the packaged medical article comprises a packaged medical adhesive article as described above, opening the package, removing the medical article from the package, unfolding the medical article, and applying the medical article to mammalian skin.

As mentioned above, the packaged medical article comprises a package enclosing the medical article, and a medical article contained within the package wherein the medical article comprises an adhesive article, and wherein the adhesive article comprises at least one fold along an axis of symmetry of the adhesive article.

In some embodiments, the adhesive article comprises at least three segments where the first segment comprises a first adhesive layer, the second segment, adjacent to the first segment, comprises a non-adhesive layer, and the third segment, adjacent to the second segment, comprising a second adhesive layer, and one fold along an axis of symmetry of the adhesive article, where the one fold is located in the second segment. The article also comprises a double-sided release liner with a first release surface and a second release surface, wherein the first release surface is in contact with the adhesive layer of the first segment, and the second release surface is in contact with the second adhesive layer of the third segment The method further comprises removing the first and second adhesive layers from the double-sided release liner.

In some embodiments, the method for preparing the packaged medical article comprises preparing an adhesive medical article, folding the adhesive medical article along an axis of symmetry of the adhesive medical article to form a folded medical article, and placing the folded medical article in a package.

Medical articles of this disclosure may be further understood by reference to the Figures. FIG. 1 shows a top view of medical article 100. Article 100 can be folded either along fold line 10 or fold line 20.

Figure 2:
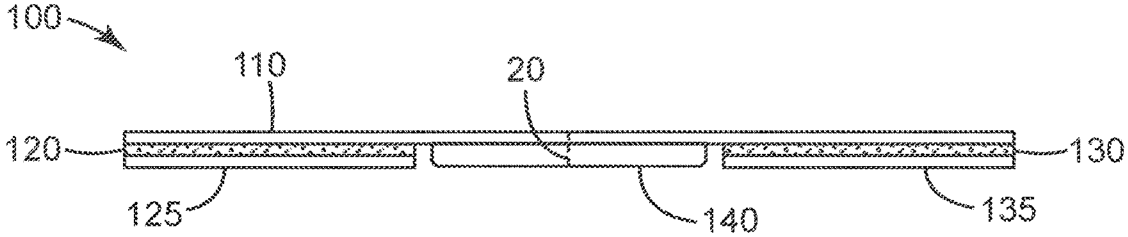
FIG. 2 is a cross-sectional view of another adhesive medical article of this disclosure.

FIG. 2 shows a cross-sectional view of article 100, showing the different segments of the article. Article 100 has backing layer 110. Disposed on backing layer 110 are two adhesive segments 120 and 130, and absorbent segment 140. Release liner 125 is disposed on adhesive segment 120 and release line 135 is disposed on adhesive segment 130. Absorbent segment 140 is bisected by fold line 20.

Figure 3:
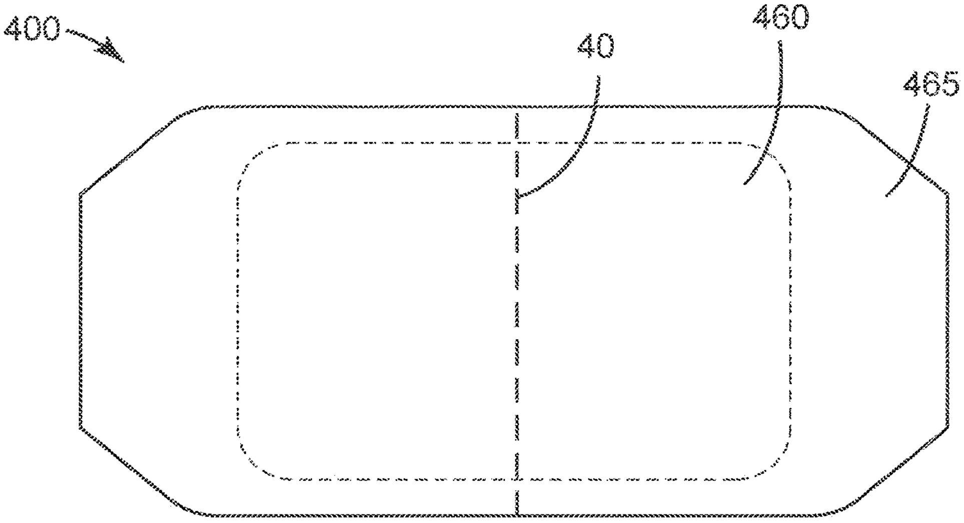
FIG. 3 is a top view of another adhesive medical article of this disclosure.

FIG. 3 shows a top view of medial article 400, looking down upon the backing layer. Removable liner segments 465 surround transparent absorbent segment 460. Fold line bisects the article.

Figure 4:
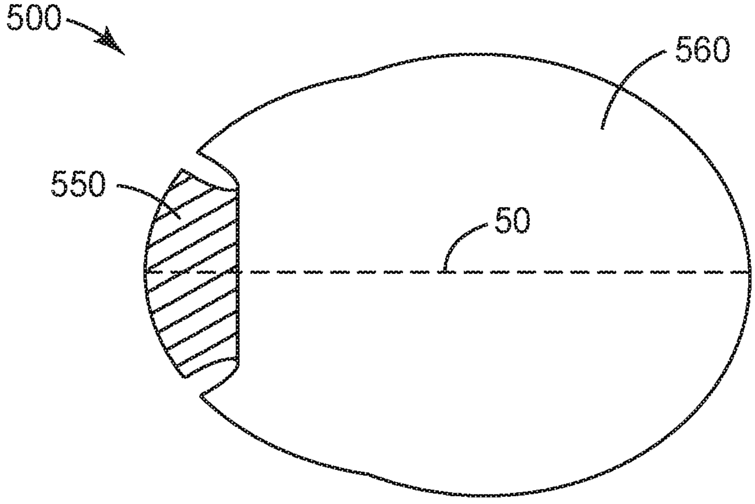
FIG. 4 is a top view of an eye patch article of this disclosure.

FIG. 4 shows a top view of eye patch article 500. Article 500 has non-adhesive region 550 and eye patch 560. Fold line 50 bisects the article.

Figure 5:
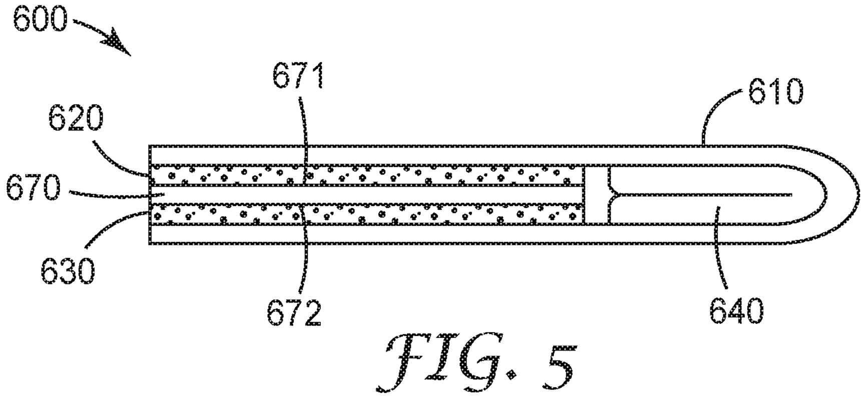
FIG. 5 is a cross-sectional view of another adhesive medical article of this disclosure.

FIG. 5 show a cross-sectional view of folded article 600. Folded article 600 has backing layer 610. Disposed on backing layer 610 are two adhesive segments 620 and 330, and absorbent segment 640. Double sided release liner 670 has release surfaces 671 and 672, where release surface 671 is disposed on adhesive segment 620 and release surface 672 is disposed on adhesive segment 630.

Figure 6:
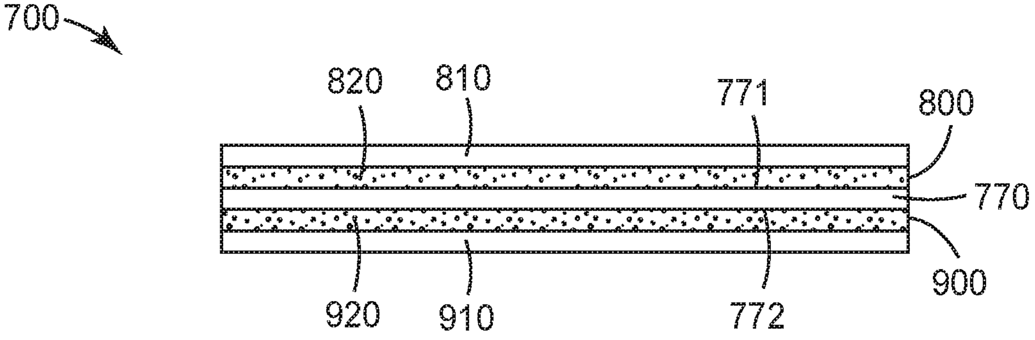
FIG. 6 is a cross-sectional view of another eye patch article of this disclosure.

FIG. 6 shows a cross-sectional view of article 700. The article 700 has two adhesive articles (800 and 900) disposed on double sided release liner 770 with release surface 771 and 772. Adhesive article 800 has backing layer 810 and adhesive layer 820. Adhesive layer 820 is disposed on release surface 771. Adhesive article 900 has backing layer 910 and adhesive layer 920. Adhesive layer 920 is disposed on release surface 772. Adhesive articles 800 and 900 may be the same or different. In some embodiments, at least one of 800 and 900 is any eye patch.

Figure 7:
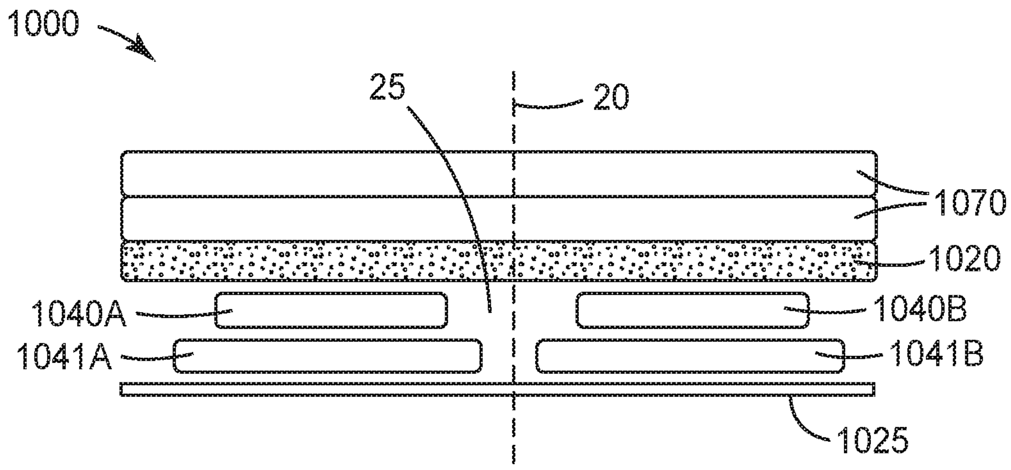
FIG. 7 is a cross-sectional view of another adhesive medical article of this disclosure.

FIG. 7 shows a cross-sectional view of article 1000. The article 1000 demonstrates a gap formed in an adhesive medical article as is described above. In article 1000, comprises backing layer 1070 (in this embodiment backing layer 1070 is shown as an optional 2-layer backing layer) with adhesive layer 1020 disposed on it. In the embodiment shown in article 1000, the article contains a 2-layer absorbent construction, layers 1040 (subdivided into subsegments 1040A and 1040B) and 1041 (subdivided into subsegments 1041A and 1051B), where layer 1040 is an absorbent pad and layer 1041 is an absorbent foam layer. The absorbent construction is bisected by fold line 20 and by gap 25. The absorbent subsections are disposed on release liner 1025. The gap aids in the folding of the article.

EXAMPLES

These examples are merely for illustrative purposes only and are not meant to be limiting on the scope of the appended claims.

TABLE of Abbreviations

| Abbreviation or Trade Designation | Description |
|---|---|
| Sample 1 | An adhesive bandage commercially available as TEGADERM + PAD ref 3586 |
| Sample 2 | An adhesive bandage commercially available as TEGADERM I.V. ADVANCED ref 1624W |
| Sample 3 | An adhesive bandage commercially available as TEGADERM I.V. ADVANCED ref 1683 |
| Sample 4 | An adhesive bandage commercially available as TEGADERM Film ref 1626W |

Sample Preparation and Testing Procedure

A general procedure was used to prepare and test samples of medical adhesive articles. A packaged adhesive article sample with the dimensions shown in Table 1 was removed from the package, folded, and placed into a new package with the dimensions shown in Table 1. The folded sample (Example E) was removed from the package, unfolded and tested by adhering to a stainless-steel plate. An identical unfolded sample (Comparative Example CE) was tested by adhering to a stainless-steel plate. The resulting adhesive attributes of the unfolded and folded samples were compared, and the result is recorded as "Unchanged" if the adhesive sample performed the same as an unfolded sample or "Different" if they behaved differently.

TABLE 1

| Example | Sample | Package Dimensions Initial | Package Dimensions After Folding | Adhesion Performance |
|---|---|---|---|---|
| E1 | Sample 1 | 19 cm × 13.5 cm | 9.5 cm × 13.5 cm | Unchanged |
| CE1 | Sample 1 | 19 cm × 13.5 cm | — | — |
| E2 | Sample 2 | 17 cm × 13 cm | 8.5 cm × 13 cm | Unchanged |
| CE2 | Sample 2 | 17 cm × 13 cm | — | — |
| E3 | Sample 3 | 17 cm × 10.5 cm | 17 cm × 5.25 cm | Unchanged |
| CE3 | Sample 3 | 17 cm × 10.5 cm | — | — |
| E4 | Sample 4 | 8 cm × 14.5 cm | 4 cm × 14.5 cm | Unchanged |
| CE4 | Sample 4 | 8 cm × 14.5 cm | — | — |

Additionally, the back section of the packages was removed, as the packages were fully self-contained after folding using only the front half of the packaging. The packages were weighed before and after removal of the package backing to show the weight decrease from the material eliminated.

TABLE 2

| Example | Sample | Package Weight Initial | Package Weight After Removal of Package Backing | Adhesion Performance |
|---|---|---|---|---|
| E1 | Sample 1 | 5.92 g | 4.32 g | Unchanged |
| E2 | Sample 2 | 2.22 g | 1.56 g | Unchanged |
| E3 | Sample 3 | 4.65 g | 3.48 g | Unchanged |
| E4 | Sample 4 | 5.84 g | 4.38 g | Unchanged |

Eye Patch Examples:

TABLE 3

| Abbreviation or Trade Designation | Description |
|---|---|
| Sample 5 | An adhesive eye patch commercially available as 3M OPTICLUDE Standard Boy in Maxi Size |
| Sample 6 | An adhesive eye patch commercially available as 3M OPTICLUDE Standard Boy in Midi Size |
| Sample 7 | An adhesive eye patch commercially available as 3M OPTICLUDE Silicone Boy in Midi Size |

Folded Eye Patches

Commercially available 3M OPTICLUDE eye patches are provided with two liners with overlap. Liner overlap was oriented along the long axis of the eye patch. Eye patches were folded along the liner overlap to reduce packaging dimensions. Dimensions before and after folding are shown in Table 4. The sample dimension can be reduced by 50% through folding without compromising the required product design for the designated application.

TABLE 4

| Example | Sample | Sample Dimensions Initial | Sample Dimensions after folding |
|---|---|---|---|
| E5 | Sample 5 | 5.7 × 8.0 cm | 2.5 × 8.0 cm |
| E6 | Sample 6 | 5.3 × 7.0 cm | 2.7 × 7.0 cm |
| E7 | Sample 7 | 5.3 × 7.0 cm | 2.7 × 7.0 cm |

Weight Reductions Through Delivery of Two Eye Patches on One (Double-Sided) Release Liner Commercially available eye patches are delivered as a single article with liners protecting the adhesive layer of each single eye patch. Through attachment of two eye patches on the opposite sides of one release liner packaging weight can be reduced. Table 5 shows data and calculation to illustrate this. Single commercially eye patches with and without release liner were weighed on a lab balance. Also, the weight of the release liner was weighed using a lab balance. Then, two eye patches were adhered to the opposite sides of one their release liner. The weight of the construction with two patches on liner was calculated according to the following formula:

Weight of two patches with one liner (grams)=(2*Sample weight of patch without liner)+Sample weight of liner.

The weight savings per eye patch have been calculated according to the following formula:

Weight savings per eye patch (%)=((((2*sample weight initial)(Weight of two patches with one liner)/(2*sample weight initial))/2)*100%.

Data for weight reductions through delivery of two eye patches on one release liner are shown in Table 5. The weights of sample weight initial, sample weight patch without liner and sample weight liner represent the average of three measurements of the same lot.

TABLE 5

| Example | Sample | Sample Weight Initial | Sample weight patch only without liner | Sample weight liner | Weight two patches with one liner | Weight savings per eye patch |
|---|---|---|---|---|---|---|
| E8 | Sample 5 | 0.828 g | 0.456 g | 0.371 g | 1.28 g | 11.3% |
| E9 | Sample 6 | 0.660 g | 0.366 g | 0.293 g | 1.02 g | 11.2% |
| E10 | Sample 7 | 0.982 g | 0.575 g | 0.406 g | 1.56 g | 10.4% |

Two Folded Eye Patches on Double-Sided Liner

One release liner of an eye patch was removed and attached to the backside of the release liner of a second eye patch. Because each eye patch contains two release liners, each of the two eye patches can now be folded along the length axis to provide two eye patches on a double-sided release liner. The weight of the construction is shown in Table 6.

The relative weight reduction of this construction has been calculated using the following formula:

Relative Weight Reduction (%)=((Weight Sum of Patch 1 and 2−Weight of Patch 1 and 2 on double-sided liner)/Weight Sum of Patch 1 and 2)*100%.

The relative packaging dimension reduction from folding each eye patch in half is 50% for all samples, as shown in Table 6.

TABLE 6

| Expl | Sample | Weight of Patch 1 | Weight of Patch 2 | Dimensions of Single Patch | Weight Sum of patch 1 and 2 | Weight of Patch 1 and 2 on double-sided liner | Dimension of two folded patches on ds-liner | Relative Weight Reduction | Relative packaging dimensions reduction |
|---|---|---|---|---|---|---|---|---|---|
| E11 | Sample 5 | 0.836 g | 0.851 g | 5.7 × 8.0 cm | 1.687 g | 1.500 g | 2.5 × 8.0 cm | 11.1% | 50% |
| E12 | Sample 6 | 0.658 g | 0.679 g | 5.3 × 7.0 cm | 1.337 g | 1.181 g | 2.7 × 7.0 cm | 11.6% | 50% |
| E13 | Sample 7 | 0.978 g | 0.979 g | 5.3 × 7.0 cm | 1.957 g | 1.736 g | 2.7 × 7.0 cm | 11.3% | 50% |

Foldability Examples of Commercial Medical Articles

A series of commercially available wound dressing articles were either folded in half to illustrate the widespread applicability of the techniques of this disclosure, or a method of folding them is proposed to prepare the folded article. A listing of the samples tested is included in Table 7.

TABLE 7

Sample List.

| Abbreviation | Description |
|---|---|
| Sample 1 | 3M TEGADERM CLEAR ACRYLIC DRESSING |
| Sample 2 | 3M MEDIPORE + PAD |
| Sample 3 | 3M TEGADERM + PAD |
| Sample 4 | S&N OPSITE VISIBLE |
| Sample 5 | BSN LEUKOMED CONTROL |
| Sample 6 | 3M TEGADERM SILICONE FOAM BORDER |
| Sample 7 | 3M TEGADERM HP FOAM DRESSING |

Examples E14-E18: 3M Tegaderm Clear Acrylic Dressing

Product Description:

3M TEGADERM CLEAR ACRYLIC DRESSING is a wound dressing for low to medium exudating wounds. The transparent absorbent pad enables the medical professional to monitor the wound during weartime.

Folding Procedure:

The commercial sample for Example E16 was folded along the middle axis to not comprise the integrity of the absorbent pad. The same folding procedure can be done for Example E14-E15, and E17-E18. The size reductions of packaged articles in this product family are shown in Table 8.

TABLE 8

| Expl | Product ID | Current Dressing Size | Dressing Size after folding | Packaging size reduction (%) |
|---|---|---|---|---|
| E14 | 90800 (Oval) | 7.6 × 9.5 cm | 7.6 × 4.8 cm | 50 |
| E15 | 90801 (Oval) | 11.1 × 12.7 cm | 11.1 × 6.3 cm | 50 |
| E16 | 90803 (Oval) | 14.2 × 15.8 cm | 14.2 × 7.9 cm | 50 |
| E17 | 90815 (Rectangle) | 9.0 cm × 25.0 cm | 9.0 × 12.5 cm | 50 |
| E18 | 90817 (Large Rectangle) | 9.0 cm × 35.0 cm | 9.0 × 17.5 cm | 50 |

Examples E19-E27: 3M Tegaderm+Pad

Product Description:

3M TEGADERM+PAD is a transparent wound dressing with a non-adherent absorbent wound contact layer.

Folding Procedure:

The dressings were easily be folded along the middle axis. In some samples, in order to enable an easier fold, the absorbent pad and the carrier can be cut along the middle axis folding line to support the fold along folding line. The size reductions of packaged articles in this product family are shown in Table 9.

TABLE 9

| Expl | Product ID | Current Dressing Size | Dressing Size after folding | Packaging reduction (%) |
|---|---|---|---|---|
| E19 | 3582 | 5.0 × 7.0 cm | 5.0 × 3.5 cm | 50 |
| E20 | 3584 | 6.0 × 10.0 cm | 6.0 × 5.0 cm | 50 |
| E21 | 3586 | 9.0 × 10.0 cm | 9.0 × 5.0 cm | 50 |
| E22 | 3587 (Oval) | 9.0 × 10.5 cm | 9.0 × 5.8 cm | 50 |
| E23 | 3588 | 15.0 × 15.0 cm | 15.0 × 7.5 cm | 50 |
| E24 | 3589 | 9.0 × 15.0 cm | 9.0 × 7.5 cm | 50 |
| E25 | 3590 | 9.0 × 20.0 cm | 9.0 × 10 cm | 50 |
| E26 | 3591 | 9.0 × 25.0 cm | 9.0 × 12.5 cm | 50 |
| E27 | 3593 | 9.0 × 35.0 cm | 9.0 × 17.5 cm | 50 |

Examples E28-E35: 3M Medipore+Pad

Product Description:

3M MEDIPORE+PAD is a Soft Cloth Adhesive Wound Dressing. The product construction is basically the same as 3M TEGADERM+PAD except that there is no product carrier and a soft-cloth material is used instead of a transparent polymeric film carrier.

Folding Procedure:

The dressings can be folded as described above for 3M TEGADERM+PAD described above. The size reductions of packaged articles in this product family are shown in Table 10.

TABLE 10

| Expl | Product ID | Current Dressing Size | Dressing Size after folding | Packaging reduction (%) |
|---|---|---|---|---|
| E28 | 3562 | 5.0 × 7.0 cm | 5.0 × 3.5 cm | 50 |
| E29 | 3564 | 6.0 × 10.0 cm | 6.0 × 5.0 cm | 50 |
| E30 | 3566 | 9.0 × 10.0 cm | 9.0 × 5.0 cm | 50 |
| E31 | 3568 | 15.0 × 15.0 cm | 15.0 × 7.5 cm | 50 |
| E32 | 3569 | 9.0 × 15.0 cm | 9.0 × 7.5 cm | 50 |
| E33 | 3570 | 9.0 × 20.0 cm | 9.0 × 10.0 cm | 50 |
| E34 | 3571 | 9.0 × 25.0 cm | 9.0 × 12.5 cm | 50 |
| E35 | 3573 | 9.0 × 35.0 cm | 9.0 × 17.5 cm | 50 |

Examples E36-E41: S&N Opsite Visible

Product Description:

The dressing is a self-adhered, transparent film layer, a honeycomb-shaped absorbent pad, and a release liner.

Folding Procedure:

For Example E36, a simple cut along the folding axis through the honeycomb-shaped foam material was made using a knife to form a folding line without compromising the product design or the integrity of the absorbent material. For Examples E37-E41 a similar cut could be made to form a folding line. The size reductions of packaged articles in this product family are shown in Table 11.

TABLE 11

| Expl | Product ID | Current Dressing Size | Dressing Size after folding | Packaging reduction (%) |
|---|---|---|---|---|
| E36 | 66800136 | 10.0 × 8.0 cm | 5.0 × 8.0 cm | 50 |
| E37 | 66800137 | 15.0 × 10.0 cm | 7.5 × 10.0 cm | 50 |
| E38 | 66800138 | 20.0 × 10.0 cm | 10.0 × 10.0 cm | 50 |
| E39 | 66800139 | 25.0 × 10.0 cm | 12.5 × 10.0 cm | 50 |
| E40 | 66800140 | 30.0 × 10.0 cm | 15.0 × 10.0 cm | 50 |
| E41 | 66800141 | 25.0 × 10.0 cm | 12.5 × 10.0 cm | 50 |

Examples E42-E46: BSN Leukomed Control

Product Description:

BSN LEUKOMED CONTROL is a transparent, absorbent wound dressing. The dressing comprises a transparent film with a transparent carrier for application support as well as several clear absorbent pads. LEUKOMED CONTROL is commercially available in a non-folded, single-packaged sterile package.

Folding Procedure:

The separated pads can easily be folded along the short edge of the dressing. The size reductions of packaged articles in this product family are shown in Table 12.

TABLE 12

| Expl | Product ID | Current Dressing Size | Dressing Size after folding | Packaging reduction (%) |
|---|---|---|---|---|
| E42 | 73230-00000-00 | 5.0 × 7.0 | 5.0 × 3.5 cm | 50 |
| E43 | 73230-00001-00 | 7.0 × 10.0 | 7.0 × 5.0 cm | 50 |
| E44 | 73230-00002-00 | 8.0 × 15.0 | 4.0 × 7.5 cm | 50 |
| E45 | 73230-00003-00 | 10.0 × 24.0 | 10.0 × 12.0 cm | 50 |
| E46 | 73230-00005-00 | 10.0 × 35.0 cm | 10.0 × 17.5 cm | 50 |

Examples E47-E53: 3M Tegaderm Silicone Foam Border

Product Description:

3M TEGADERM SILICONE FOAM BORDER is a highly absorbent wound dressing, which is gentle-to-skin with a long wear time.

Folding Procedure:

For foam Dressings, where the absorbent pad is not in direct contact with the wound, but a perforated skin-contact layer is in contact with the skin/wound area to allow the wound exudate to pass through into the absorbent, folding is not straight forward. In addition, the foam area is rather thick, which makes folding difficult. Also, making a simple cut through the absorbent pad (as shown in some of the previous examples, e.g. MEDIPORE+PAD) is not suitable, because this could destroy the multilayer-absorbent construction and allow for direct wound contact of the absorbent layers underneath the foam. Therefore, in these conceptual examples, two separate absorbent areas can be implemented in the dressing that are sandwiched separately, which enables a clear fold along the middle axis, while maintaining the integrity of the absorbent pad (incl. its supporting layers) in the folded and in the de-folded state. The size reductions of packaged articles in this product family are shown in Table 13.

TABLE 13

| Expl | Product ID | Current Dressing Size | Dressing Size after folding | Packaging reduction (%) |
|---|---|---|---|---|
| E47 | 90643 | 5.0 × 5.0 cm | 5.0 × 2.5 cm | 50 |
| E48 | 90640 | 8.0 × 8.0 cm | 8.0 × 4.0 cm | 50 |
| E49 | 90641 | 10.0 × 10.0 cm | 10.0 × 5.0 cm | 50 |
| E50 | 90642 | 15.0 × 15.0 cm | 15.0 × 7.5 cm | 50 |
| E51 | 90646 (Heel) | 15.0 × 15.0 cm | 15.0 × 7.5 cm | 50 |
| E52 | 90647 (Sacral) | 15.0 × 17.0 cm | 15.0 × 8.5 cm | 50 |
| E53 | 90648 (Sacral) | 18.5 × 22.0 cm | 18.5 × 11.0 cm | 50 |

Examples E54-E61: 3M Tegaderm HP Foam Dressing

Product Description:

3M TEGADERM HP FOAM DRESSING has a multilayer design, which provides high absorbency with high breathability to reduce the risk of maceration.

Folding Procedure

Due to the two absorbent layers of the absorbent pad, a clean cut is not sufficient to enable a folded dressing. To solve this problem, a new dressing design is proposed having two distinct absorbent foams (+pad above) on each side of the foam, enabling a clean fold along the middle axis in the thin TEGADERM film. Two separate carrier layers further enhance the easy-to-use properties of the proposed folded dressing. The size reductions of packaged articles for this proposed product family are shown in Table 14.

TABLE 14

| Expl | Product ID | Current Dressing Size | Dressing Size after folding | Packaging reduction (%) |
|---|---|---|---|---|
| E54 | 90610 (square) | 8.8 × 8.8 cm | 8.8 × 4.4 c | 50 |
| E55 | 90611 (oval) | 10.0 × 11.0 cm | 10.0 × 5.5 cm | 50 |
| E56 | 90612 (square) | 14.3 × 14.3 cm | 14.3 × 7.15 cm | 50 |
| E57 | 90613 (oval) | 14.3 × 15.6 cm | 14.3 × 7.8 cm | 50 |
| E58 | 90614 (oval) | 6.9 × 7.6 cm | 6.9 × 3.8 cm | 50 |
| E59 | 90616 (oval) | 19.0 × 22.2 cm | 19.0 × 11.1 cm | 50 |
| E60 | 90619 (heel) | 14.0 × 14.0 cm | 7.0 × 7.0 cm | 50 |
| E61 | 90615 (mini wrap) | 6.9 × 6.9 cm | 6.9 × 3.45 cm | 50 |

What is claimed is:

1. A system comprising:

a package; and a medical article contained within the package wherein the medical article comprises an adhesive article, comprising:

a backing layer;

a first segment comprising a first adhesive layer disposed on the backing layer;

a second segment, adjacent to the first segment, comprising an absorbent pad disposed on the backing layer; and a third segment, adjacent to the second segment, comprising a second adhesive layer disposed on the backing layer;

one fold along a fold line along an axis of symmetry of the adhesive article and located in the second segment, wherein the fold bisects the absorbent pad; and a double-sided release liner with a first release surface and an opposing second release surface, wherein the first release surface is in contact with the first adhesive layer of the first segment, and the second release surface is in contact with the second adhesive layer of the third segment.

2. The system of claim 1, wherein the first adhesive layer and the second adhesive layer independently comprise a pressure sensitive adhesive layer or a gel adhesive.

3. The system of claim 1, wherein the first release surface of the double-sided release liner is the same as the second release surface.

4. The system of claim 1, wherein the first release surface comprises a first release coating and the second release surface comprises a second release coating and the first release coating is different from the second release coating.

5. A system comprising:

a package; and a medical article contained within the package, wherein the medical article comprises:

a double-sided release liner with a first release surface with a first release coating and an opposing second release surface with a second release coating, wherein the first and second release coatings are different;

a first adhesive article attached to the first release surface of the double-sided release liner;

a second adhesive article attached to the second release surface of the double-sided release liner; and wherein the second adhesive article is independent from the first adhesive article.

6. The system of claim 5, wherein the first adhesive article and the second adhesive article are the same.

7. The system of claim 6, wherein the first and second adhesive articles comprise eye patches.

8. The system of claim 5, wherein the first adhesive article and the second adhesive article are different.

* * * * *